United States Patent
Black

(10) Patent No.: US 9,345,585 B2
(45) Date of Patent: May 24, 2016

(54) ACETABULAR CUP INSERTION INSTRUMENTS

(71) Applicant: Howmedica Osteonics Corp., Mahwah, NJ (US)

(72) Inventor: Brandon Black, Hoboken, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 296 days.

(21) Appl. No.: 14/048,549

(22) Filed: Oct. 8, 2013

(65) Prior Publication Data

US 2015/0100060 A1 Apr. 9, 2015

(51) Int. Cl.
*A61F 2/46* (2006.01)
*A61F 2/30* (2006.01)

(52) U.S. Cl.
CPC ............... *A61F 2/4609* (2013.01); *A61F 2/46* (2013.01); *A61F 2/4603* (2013.01); *A61F 2002/30079* (2013.01); *A61F 2002/30331* (2013.01); *A61F 2002/30471* (2013.01); *A61F 2002/4629* (2013.01); *A61F 2002/4681* (2013.01)

(58) Field of Classification Search
CPC .... A61B 17/56; A61B 17/88; A61B 17/8872; A61B 17/92; A61B 2017/922; A61F 2/46; A61F 2/4603; A61F 2/4609; A61F 2002/4629; A61F 2002/30079
See application file for complete search history.

(56) References Cited

U.S. PATENT DOCUMENTS

| | | | |
|---|---|---|---|
| 4,023,572 A | 5/1977 | Weigand et al. | |
| 5,431,657 A * | 7/1995 | Rohr | A61F 2/4609 606/91 |
| 5,658,290 A | 8/1997 | Lechot | |
| 6,475,243 B1 | 11/2002 | Sheldon et al. | |
| 7,621,921 B2 * | 11/2009 | Parker | A61F 2/34 606/91 |
| 2003/0050645 A1 | 3/2003 | Parker et al. | |
| 2003/0229356 A1 | 12/2003 | Dye | |
| 2004/0087958 A1 | 5/2004 | Myers et al. | |
| 2004/0153063 A1 | 8/2004 | Harris | |
| 2005/0038443 A1 | 2/2005 | Hedley et al. | |
| 2005/0216022 A1 | 9/2005 | Lechot et al. | |
| 2007/0225725 A1 * | 9/2007 | Heavener | A61F 2/4609 606/91 |
| 2013/0226186 A1 * | 8/2013 | Burgi | A61B 17/56 606/91 |

OTHER PUBLICATIONS

Propsed Direct Anterior, Surgical Technique, Stryer 2013.

* cited by examiner

*Primary Examiner* — Larry E Waggle, Jr.
(74) *Attorney, Agent, or Firm* — Lerner, David, Littenberg, Krumholz & Mentlik, LLP

(57) ABSTRACT

An acetabular cup shell insertion system is provided for a shell having a threaded central opening and a part-spherical inner surface. The system includes an impactor having a strike plate at a first end and a first connection element at a second end. Also provided is a longitudinally extending adapter having a threaded first end adapted to threadably engage the threaded central opening in the acetabular cup. A second end of the adapter has a second connection element for engaging the impactor first connection element. An impaction flange extends radially outwardly of a longitudinal axis of the adapter. The flange has a first contact surface facing the second end of the adapter. A second contact surface surrounding the threaded first end of the adapter contacts the part-spherical inner surface of the acetabular cup surrounding the threaded central opening.

23 Claims, 10 Drawing Sheets

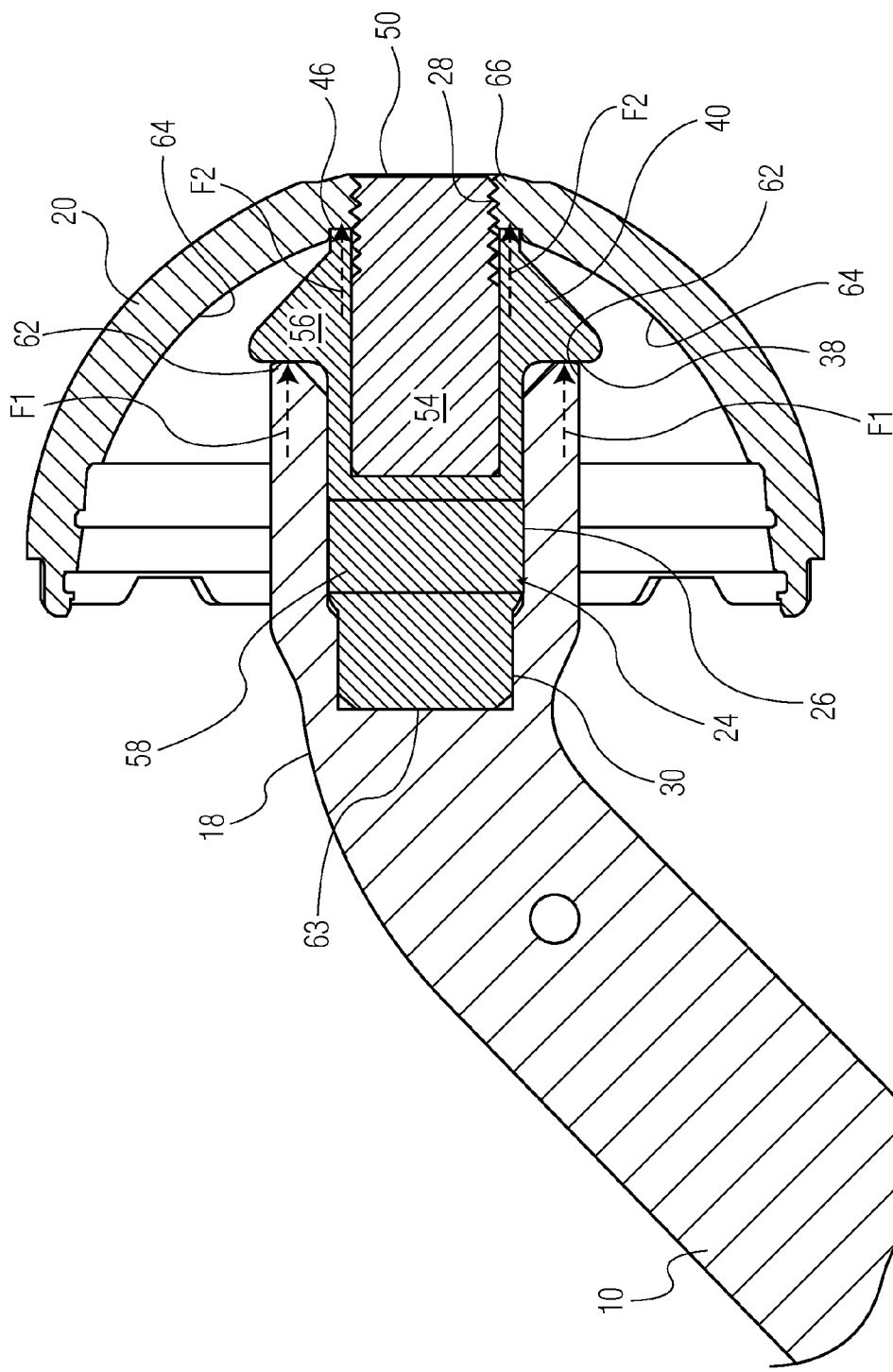

ACETABULAR CUP INSERTION INSTRUMENTS

BACKGROUND OF THE INVENTION

Over time the surgical technique for total hip replacements has evolved. Incision length has been reduced over time as surgeons become more comfortable operating with limited visibility. The location of the incision has also been changing as surgeons have developed and implemented different approaches to the joint. These two factors have increased the challenges of implanting acetabular implants in the correct orientation as the acetabular tools impinge on bone or soft tissue around the perimeter of the incision.

The present invention relates to a prosthetic acetabular cup inserter and impactor, for use particularly, but not exclusively, in minimal invasive surgery (MIS) with a short incision and/ or with an anterior approach.

Prosthetic acetabular cup inserter and impactors are used to implant prosthetic acetabular cups into the cavity of a patient's hip, and generally comprise an elongate straight or curved body with a cup engaging head at a first end thereof, and a handle and impaction plate or anvil at a second end thereof. The surgeon releasably fits a cup implant to the cup engaging head, and then positions the cup inside the patient's hip. He then applies a hammering force to the impaction anvil to secure the cup in place, before releasing the cup from the cup engaging head.

In Minimally Invasive Surgery (MIS) or in an anterior approach, it is common to use an inserter and impactor with a curved body, which is shaped to minimize impingement to the patient's soft tissue when it is inserted. In many cases the cups have irregular shapes and/or holes which have to be aligned inside the patient at a particular angle. With such constructions it is important to axially align the cup correctly in relation to the body of the inserter and impactor prior to insertion, so it is properly aligned with the patient's hip when the curved body is inserted as desired.

Acetabular implants normally consist of a shell or cup and a modular insert that fits within the shell and acts as a bearing surface for the femoral head. Such shells and inserts are shown in U.S. Pat. No. 6,475,243, the disclosure of which is incorporated herein by reference. While modular shells and inserts are preferred for a number of reasons, there is an application where shells and inserts are combined preoperatively in a monoblock construction.

Acetabular instruments normally consist of a series of reamers, a reamer handle, a shell positioner/impactor and an insert positioner/impactor. In addition, alignment guides are often attached to the reamer handle and shell positioner/ impactor in order to facilitate alignment. A typical reamer is shown in U.S. Pat. Nos. 4,023,572 and 5,658,290.

Shells are implanted into an acetabulum after the acetabulum has been prepared to receive the shell usually through the use of a series of reamers increasing in size. The shells are aligned in the acetabulum according to two angles: abduction and anteversion. The combination of these two angles creates the axis that the shell should be aligned and impacted on.

Traditionally acetabular reamer handles and shell and insert positioner/impactors had straight shafts. In some surgeries the size or location of the incision results in the shaft of these instruments impinging on the side of the incision before the preferred abduction/anteversion axis is achieved. In these cases the surgeon has to force the soft tissue or bone out of the way, increase the length of the incision, or accept the abduction/anteversion angle that can be achieved. None of these options are preferred.

One method for avoiding impingement between these acetabular instruments and the incision is to create "inline" or offset curved acetabular instruments. "Inline" refers to an acetabular instrument that has a curved section between the two ends of the instrument that lie on the same axis. Typically, with regard to reamers, the first end includes a hex connection for connection to a rotary power service (drill) and a second end which has a holder for an acetabular instrument such as a reamer or the acetabular shell or a connector for the shell. "Offset" refers to an acetabular instrument that has a curved section between the two ends of the instrument that lie on different axis. The curved section should begin as quickly as possible after the attachment to the reamer, shell impactor or inserter in order to minimize the impingement.

An inline curved acetabular instrument is preferred for a number of reasons. Typically, the surgeon is used to operating with inline straight instruments. By maintaining the inline aspect of the design, the ergonomics of the instrument remain the same and the surgeon learning curved is reduced. In addition an inline instrument allows for all forces to be projected in line or parallel to the correct axis. Having the instrument inline is very important when used as an inserter/impactor to reduce the moments that result. Finally, an inline instrument allows for alignment guides to be indexed around the axis of the instrument without changing its position in relation to the implant. In-line or offset reamers and impactors are shown in U.S. patent publications 2003/0050645, 2003/0229356, 2004/0153063, 2004/0087958, 2005/ 0038443 and 2005/0216022.

Shells are typically connected to positioner/impactors by threading the two together with torque. This is accomplished through the use of a straight shaft with a handle that the surgeon grips on one end and a threaded fitting that connects to the shell on the other end. The torque is transmitted from the surgeon to the handle to the shaft to the threaded fitting to the shell. Typically the acetabular cup shell is metal with a hemi-spherical shape. A threaded central hole is located at the pole of the hemisphere. The threaded tip of the inserter/ impactor engages this threaded bore. The axial force is transmitted from the surgeon to the mallet to the handle, to the shaft, to the threaded connector and to the pole area of the metal shell.

With an inline or offset curved acetabular instrument the axial load needs to be transmitted around a curve. In addition, the curved body that transmits the axial load cannot also transmit the torque. This is because the curved body would impinge on the incision if one tried to rotate it through a full rotation.

The curved body is preferably machined from a solid block referred to as a monoblock, to produce the curved body rather than using a bent tube. This allows the formation of an I-BEAM for increased stiffness and therefore precision because of I-BEAM construction.

BRIEF SUMMARY OF THE INVENTION

One aspect of the invention is to provide an acetabular cup inserter/impactor which permits the simple use of several instruments which can selectively couple thread an adapter into a threaded bore of an acetabular cup shell. The adapter is designed to spread the impaction load over a wide area.

Such an aspect is achieved by an acetabular cup insertion system for an acetabular cup having a threaded central opening and a part-spherical inner surface. The system is made of several parts including an impactor having a strike plate at a first end thereof and a first connection element at a second end thereof. The system also includes a longitudinally extending adapter having a threaded first end adapted to threadably engage the threaded opening in the acetabular cup shell. A second end of the adapter has a second connection element for engaging the impactor first connection element. An impaction flange extends radially outwardly of a longitudinal axis of the adapter. The flange has a first annular contact surface facing the second end of the adapter and a second annular contact surface surrounding the threaded first end of the adapter for contacting the part-spherical inner surface of the acetabular cup surrounding the threaded central opening. The distance between the first and second ends of the adapter preferably being less than the distance between the part-spherical inner surface surrounding the threaded central opening and a rim of the acetabular cup surrounding the cup inner surface.

The first and second connection elements are corresponding multi-faceted connection elements. The multi-faceted connection elements may be polygonal, for example, hexagonal in shape.

The first connection element may be located in a female socket coupled to or formed integral with the impactor second end that receives the second end of the adapter. The socket has a base portion and an open end portion for receiving the second connection element of the adapter and at least partially receives a shaft portion of the adapter, wherein the multi-faceted first connection element is located in the base portion of the socket.

The adapter may have a magnet received within a recess located adjacent the second end thereof. The adapter is made of a non-magnetic material and the impactor is made of a magnetic material. The magnet is strong enough to hold the adapter within the socket during use.

The impaction flange has a planar circular surface forming the first contact surface facing the second end of the adapter. The flange is supported by a conical portion tapering inwardly towards a central axis of the adapter and towards the first end of the adapter. The conical portion terminates in the annular surface facing the adapter first end and forming the second contact surface which bears against the inside of the metal shell. A driving tool is provided having a U-joint with connection element coupled thereto at a first end for connecting to the adapter second connection element. The connection tool has a socket similar to that described above for imparting a rotation to the adapter about a longitudinal axis thereof. This tool may be used to couple and de-couple the adapter to and from the threaded central bore of the acetabular cup shell. Coupling the two parts can also be done by hand.

These aspects can also be achieved by an acetabular cup insertion system for an acetabular cup having a threaded central opening and an inner surface. The system includes an impactor having a shaft with a strike plate at a first end thereof and a first connection element at a second end thereof, the first connection element having a first contact surface at an end thereof. An adapter is provided having a threaded first end adapted to threadably engage the central opening in the acetabular cup and a second end with a second connection element thereon. The first end has a second contact surface for contacting the inner surface of the acetabular cup. The adapter has a third contact surface facing the second end of the adapter, such that upon engagement of the first and second connection elements the second and third contact surfaces engage.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

FIG. 5 is an enlarged view potentially in cross-section, of the engagement between the leading end of the curved impactor of FIG. 1 and the adapter of FIG. 4 showing the transfer of the impaction forces to the metal shell of the acetabular cup;

DETAILED DESCRIPTION

Figure 1:
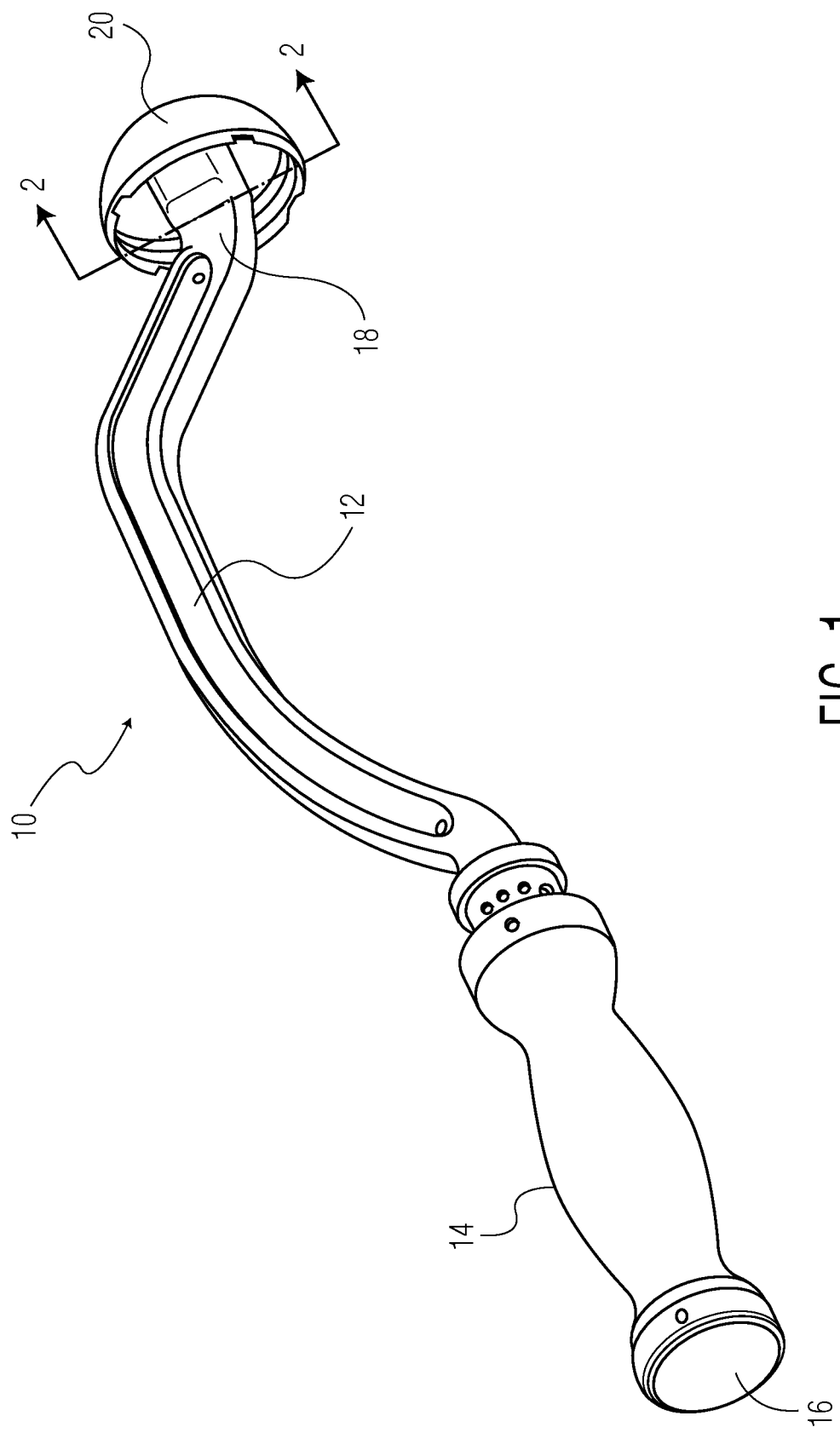
FIG. 1 is a isometric view of an acetabular cup insertion/impaction instrument including the adapter of the present invention mounted on a leading end thereof and engaged with an acetabular cup.

Referring to FIG. 1 there is shown an isometric view of a first embodiment of the inserter/impactor of the present invention generally denoted as 10. The impactor 10 includes a curved shaft 12, a handle 14, which includes at a first end thereof a strike plate 16. Shaft 12 may have a cross-section similar to an I-Beam and can either be forged or machined out of a solid rod or bar. Inserter/impactor 10 includes a leading second end 18 which is coupled to an acetbular cup shell 20 by an adapter 24 shown in FIG. 2. Typically shell 20 is made of a cobalt chrome molybdenum alloy, titanium alloy or titanium. Such a shell 20 may be of any well-known design for example that shown in U.S. Pat. No. 6,475,243.

Figure 2:
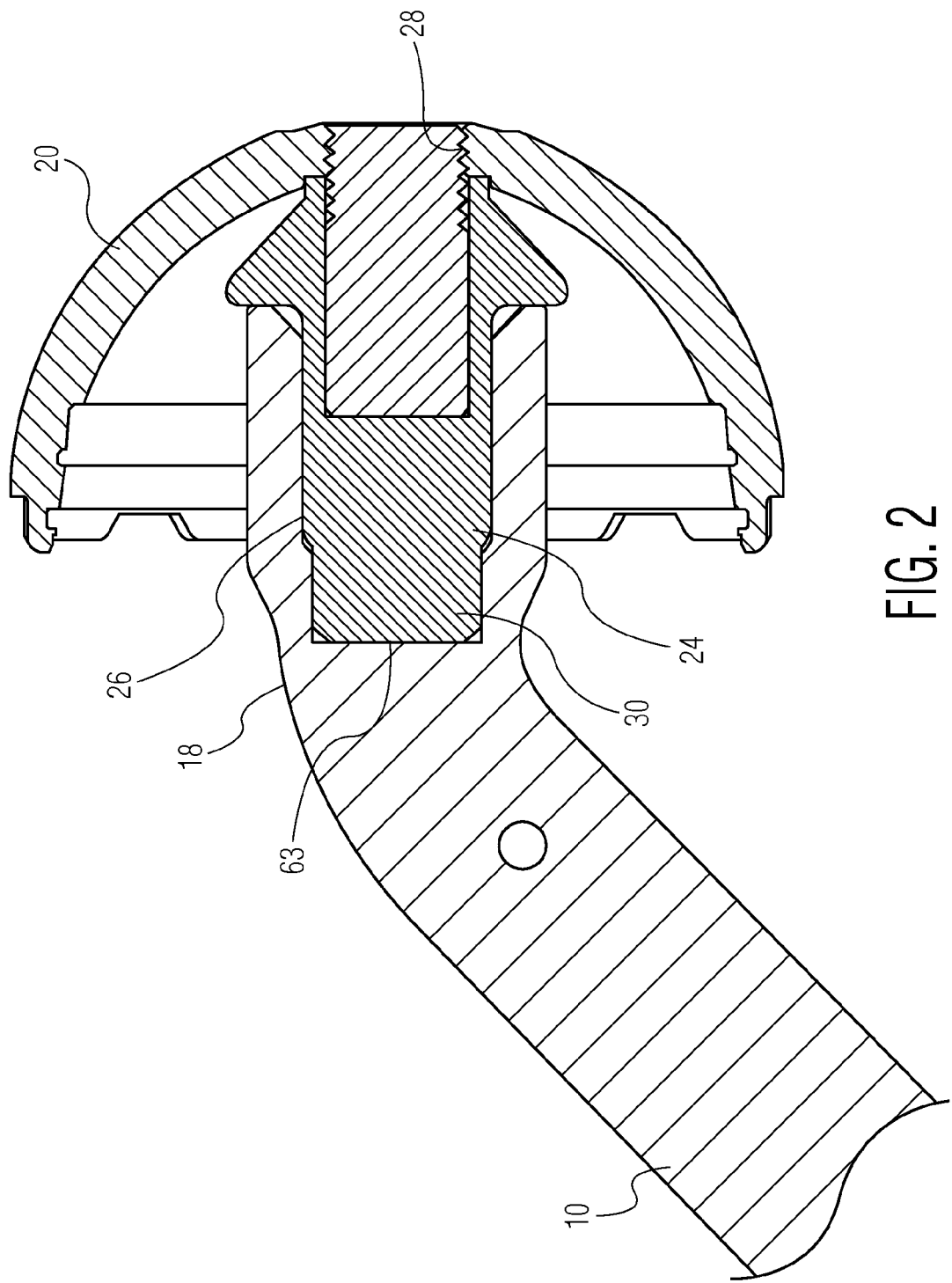
FIG. 2 is an enlarged cross-sectional view of the leading end of the instrument of FIG. 1 along lines 2-2.

Referring to FIG. 2 there is shown an enlarged view of end 18 of inserter/impactor 10. FIG. 2 is a cross-sectional view along lines 2-2 of FIG. 1. FIG. 2 shows adapter 24 inserted into a female socket 26 formed in leading end 18 of inserter/impactor 10. As will be discussed below, adapter 24 includes a threaded first end 28 and a second end 30 with a connection element formed thereon as best seen in FIGS. 4-4C.

Figure 3:
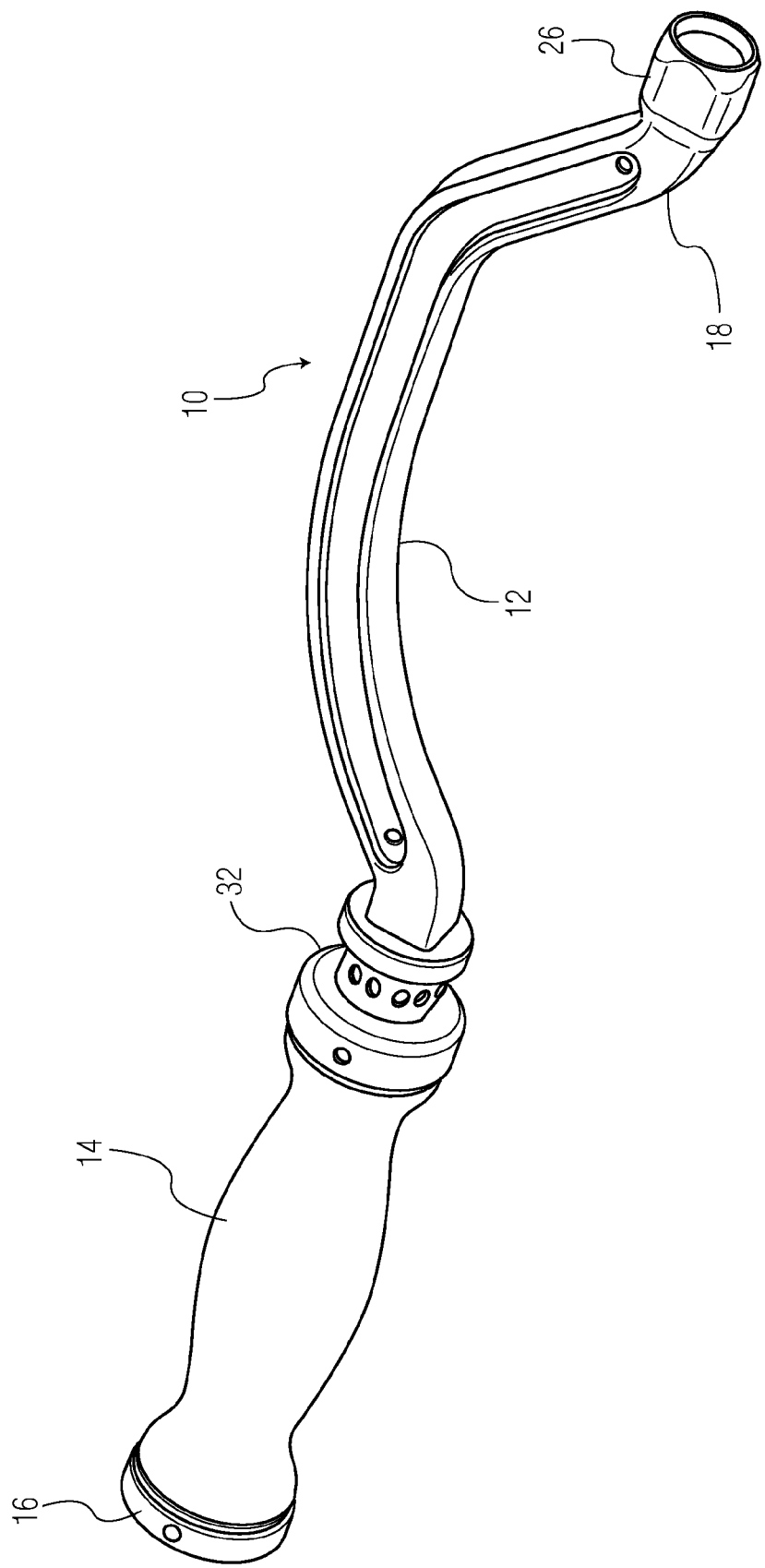
FIG. 3 is an isometric view of a curved acetabular cup inserter/impactor including a connection element at the leading end thereof.

Referring to FIG. 3 there is shown an isometric view of the inserter/impactor 10 of FIG. 1 including handle 14, impaction plate 16 and socket 26 at leading end 18. As shown in FIG. 3 there is a rotatable coupling 32 between handle 14 and shaft 12 of inserter/impactor 10. Such rotatable couplings are well-known in the art.

Figure 4:
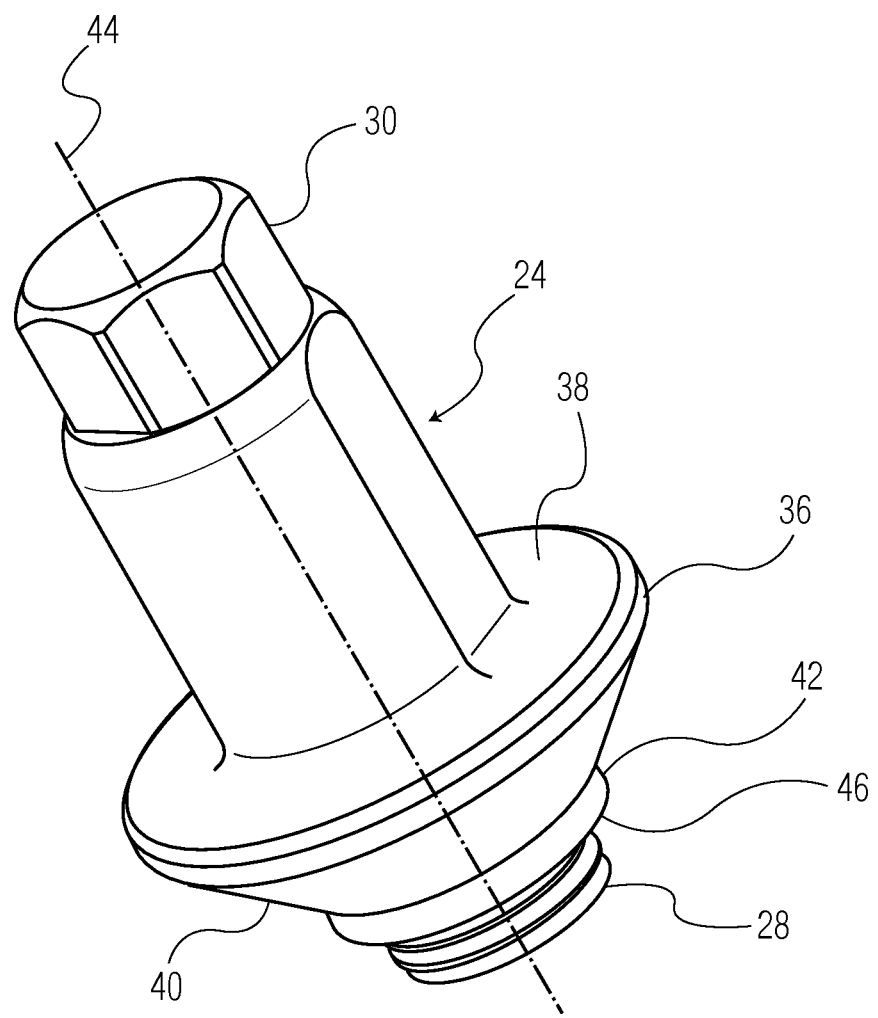
FIG. 4 is an isometric view of an adapter of the present invention capable of interconnecting the leading end of the inserter/impactor of FIG. 3 to an acetabular cup shell having a threaded central bore.

Referring to FIG. 4 there is an isometric view of adapter 24 of FIG. 2 which extends about a central longitudinal axis 44. Adapter 24 includes threaded first end 28 and connection element 30 at the second thereof. Connection element 30 may be a male polygonal connection element, for example a hexagonal connection element, or may of any other shape such as having a plurality of ridges to engage a female connection socket 26 on leading end 18 of the inserter/impactor 10. Of course, the male and female elements could be reserved with the socket 26 being on the impactor. Adapter 24 includes a conical flange 36 having a planar annular surface 38 facing the second end of the adaptor. Surface 38 is followed by an inwardly conically tapered portion 40 which terminates in a cylindrical portion 42. Tapered portion 40 tapers inwardly towards axis 44 which is the central longitudinal axis of adapter 24. Cylindrical portion 42 defines an annular end surface 46 which faces the first end of adapter 24. The outer surface of cylindrical is threaded with threads 28. Preferably both surfaces 38 and 46 are planar and extend perpendicular to axis 44.

Figure 4A:
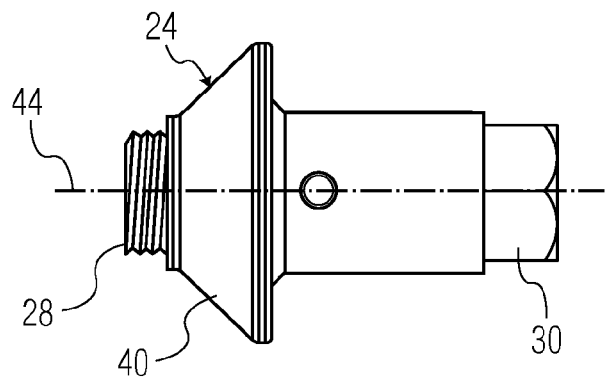
FIGS. 4A-4C show respectively a side view, an end view and a cross-sectional view along lines 4-4C of FIG. 4B, of the adapter of FIG. 4.
Figure 4B:
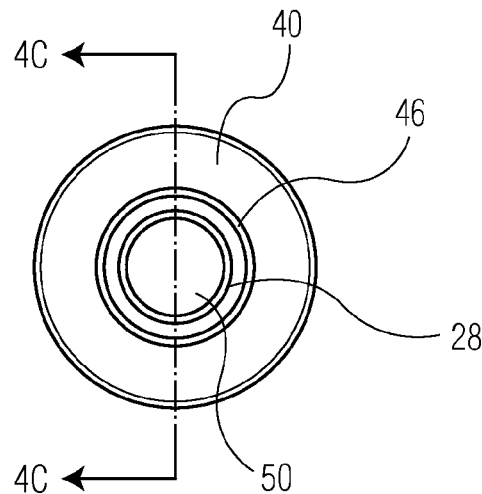
Figure 4C:
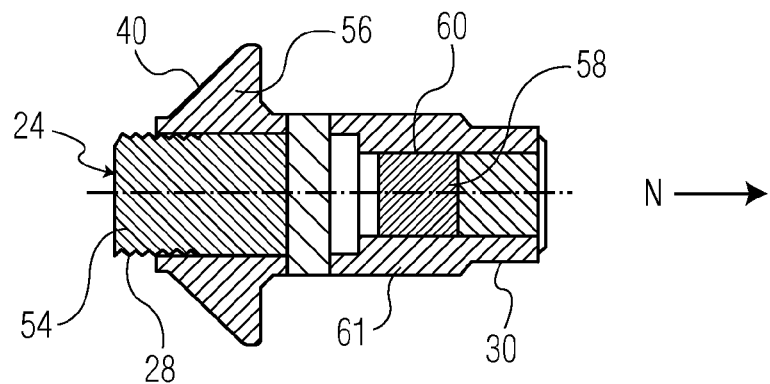

Referring to FIG. 4A there is shown an elevation or side view of the adapter 24 of FIG. 4. Referring to FIG. 4B there is shown an end view of FIG. 4A showing in the first end with thread 28, annular surface 46 and conically tapered surface 40. Also shown is a planar end surface 50. As shown in FIG. 4B the thread terminates in planar surface 50 which is located at the end of the cylindrical surface on which thread 28 is formed. Note that as shown in FIGS. 4-4C adapter 24 is not cannulated, however, a central bore surrounding axis 44 could be provided so that a guide wire could be utilized. Obviously the inserter/impactor 10 in that case would also be cannulated. Referring to FIG. 4C there is shown a cross-sectional view of the adapter 24 along lines 4C-4C of FIG. 4B. From the cross-sectional view it can be seen that the threaded portion 28 is formed on a cylindrical outer surface 54 which is press fit or welded into a hollow cylindrical inner bore 60 of a machined element 56 including flange 40. Bore 60 is formed in an extension portion 61 of element 56 which extends to the second end of the adapter. Connection element 30 is formed on extension 61. Also shown in FIG. 4C is a magnet 58 which is located adjacent to the second end of the adapter and is located within cylindrical inner bore 60 of flanged portion 56. Preferably flanged portion 56 including extension portion 61 are made of a non-magnetic material whereas the inserter/impactor socket 26 is made of a magnetizable material. Thus when adapter 24 is mounted on end 18 of inserter/impactor 10 they are held together in the axial direction by the magnetic force. As shown in FIG. 4C in the preferred embodiment the north end of the magnet is located towards the second end of the adapter 24.

Referring to FIG. 5 there is an enlarged view of end 18 similar to that shown in FIG. 2 but showing the force transmission upon impaction between inserter/impactor 10 and adapter 24 as well as the force between the adapter 24 and acetabular cup outer shell 20. The socket and adapter are so designed that a base 63 of socket 28 is spaced from end 50 of adapter 24 upon assembly. As can be seen in FIG. 5 when adapter 24 is seated within socket 26 of the leading end 18 of inserter/impactor 10 an impaction force F1 may act between an annular end surface 62 of socket 26 at leading end 18 of the impactor and surface 38 of adapter 24. This force designated as F1 in FIG. 5 is then transmitted to inner surface 64 of acetabular shell 20 by annular surface 46. This force transmission by surface 46 is shown by the arrows designated F2 in FIG. 5. Since the force F2 is transmitted at an area located radially outwardly of the central threaded hole 66 of shell 20 no force is transmitted to threaded central hole 66 of cup 20 by threads 28. This avoids a situation where the two sets of engaging threads could be deformed by the impaction making it impossible to remove adapter 24 from shell 20. Furthermore, because of tapered surface 40, there is sufficient material to resist the force F1 transmitted by annular surface 62 as it impacts against surface 38 of portion 56 of adapter 24.

Figure 6:
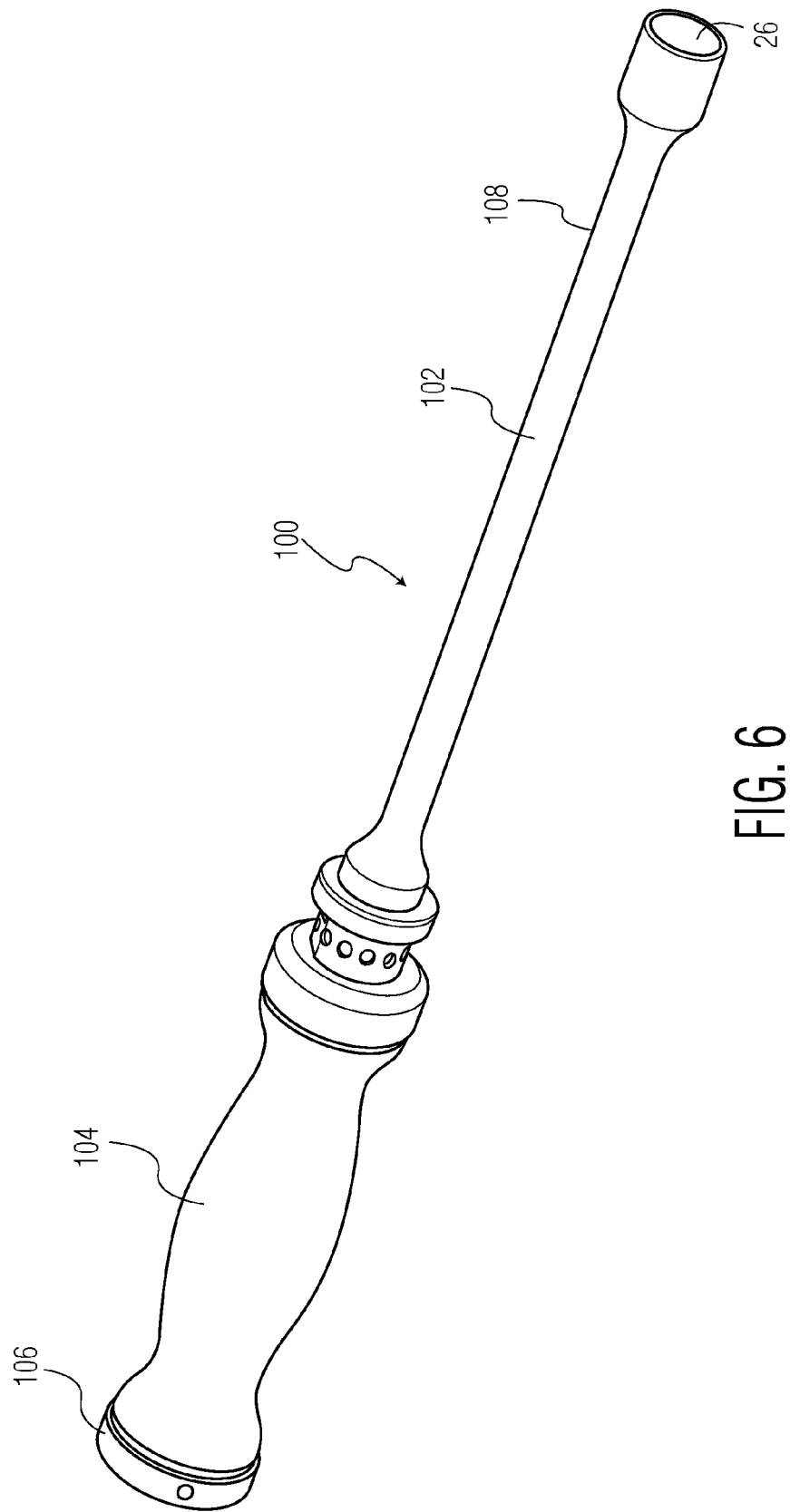
FIG. 6 is an isometric view of an alternate cup inserter/impactor having a straight shaft but including the same connection element at the leading end thereof as the inserter/impactor of FIG. 1.

Referring to FIG. 6 there is an alternate acetabular shell inserter/impactor generally designated as 100 including a shaft 102, a handle 104, an impaction plate 106 and a connection element 26 at leading end 108 of the inserter/impactor 100. The only difference between the inserter/impactor 10 and 100 is that the shafts 12 is curved and the shaft 102 is straight. The socket 26 is identical on both inserter/impactors 10 and 100. It is up to the surgeon to choose which inserter/impactor would best suit the situation.

Figure 6A:
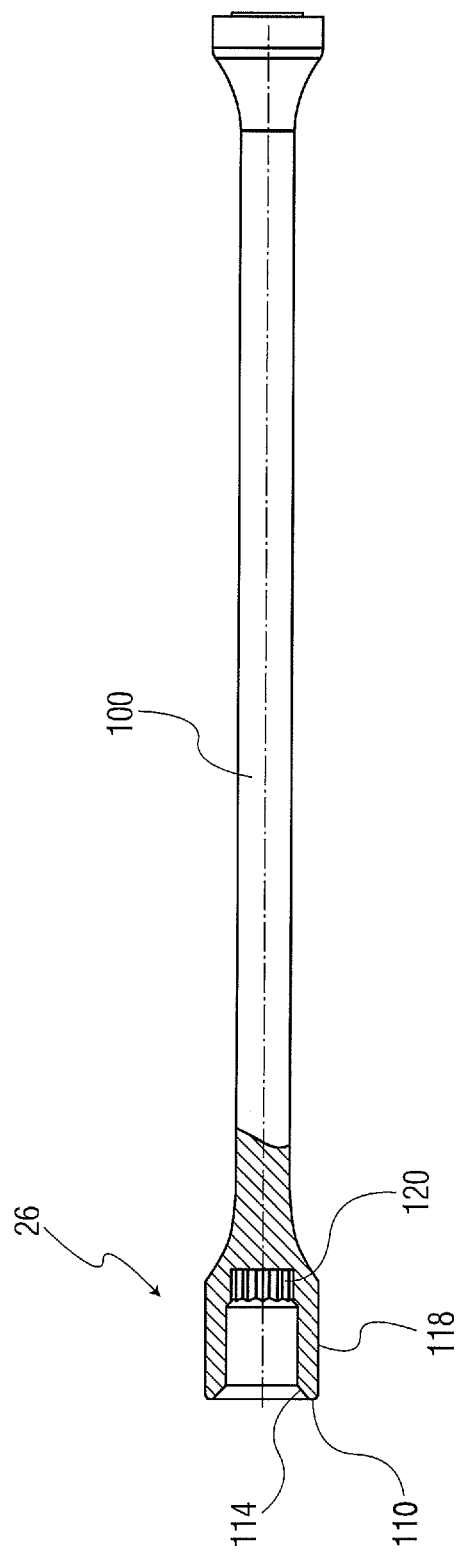
FIG. 6A is an elevation view of the impactor/inserter of FIG. 6 showing the leading end in cross-section.
Figure 6B:
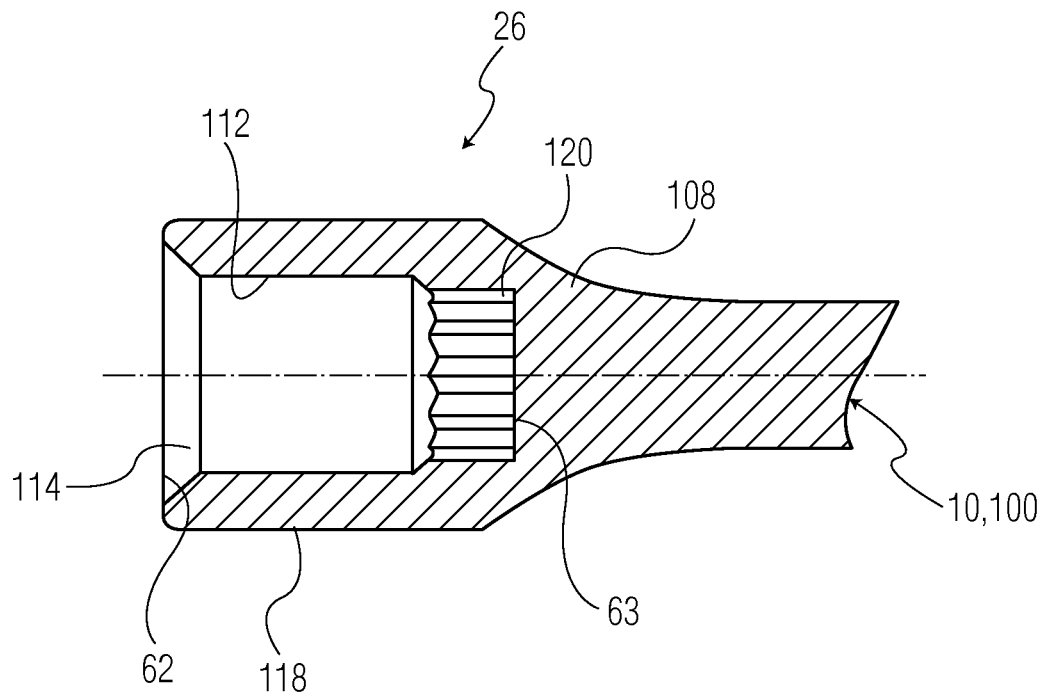
FIG. 6B is an enlarged view of the connection element at the leading end of the inserter/impactor of FIG. 1, FIG. 6 and FIG. 6A.
Figure 6C:
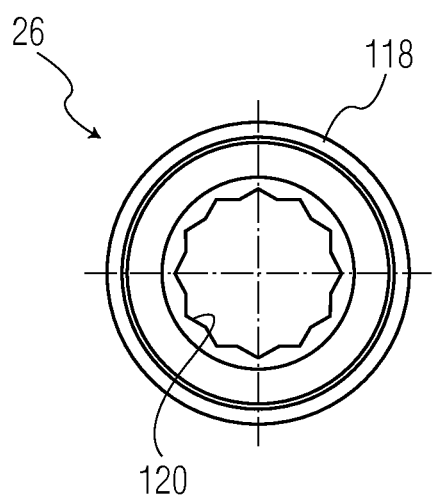
FIG. 6C is an end view of the connection element of 6B.

Referring to FIG. 6A and in particular at FIG. 6B there is shown the leading or second end of either impactor 10 or 100 generally denoted as 110. For simplicity end 110 is shown on inserter/impactor 100 in FIG. 6A. FIG. 6B shows an enlarged view of the leading end of impactor 100 showing socket 26 with FIG. 6C showing an end view of the enlarged view of FIG. 6B. As can been seen in FIG. 6A through FIG. 6C the socket 26 which couples to the connection end 30 of adapter 24 has a cylindrical inner bore 112 including an open end 114 which defines the annular contact surface 62 extending between the inner bore 112 and outer surface 118 of leading end of socket 26. When coupled to adaptor 24 inner surface 112 of socket 26 surrounds the outer surface of extension portion 56 which extends from surface 38 towards the second end of adapter 24 which extension portion includes connection element 30. At the base 63 of bore 112 is located a connection element which as shown is a multi-faceted connection 120 adapted to engage the preferably hexagonal connection 30 of adapter 24. Of course, connection 120 could also be a hexagonal female socket for driving the hexagonal male connection element of adapter 24, however using a multi-faceted connection element allows for a finer adjustment especially when using the curved inserter/impactor 10. For example, if a hexagonal connection 120 were used, the angular adjustment would be 60 degrees whereas a 12 point multi-faceted connection could be adjusted at 30 degree increments. Thus there would be twice as many angular positions when coupled to an inserter/impactor 10 with a curved shaft 12.

Figure 7:
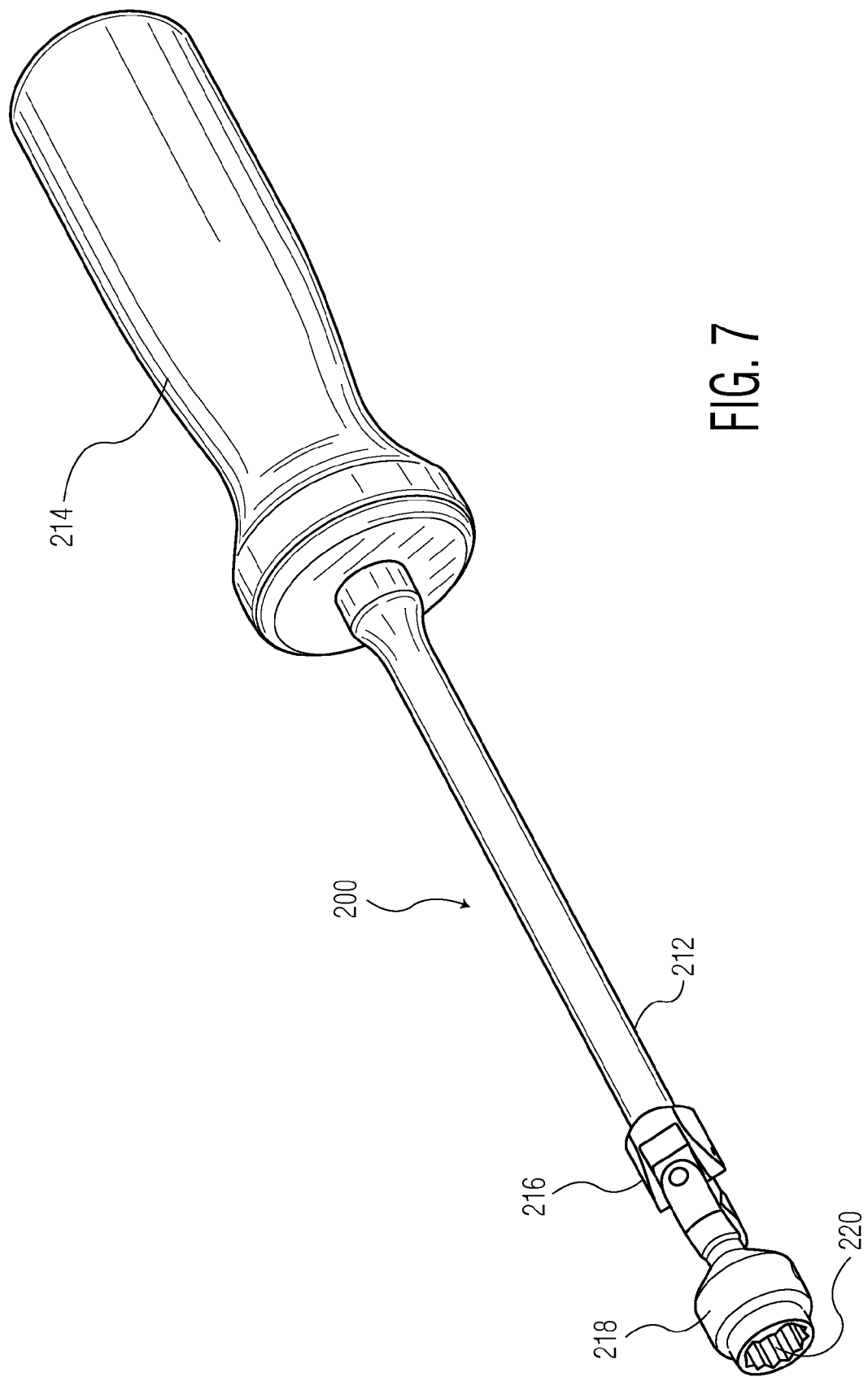
FIG. 7 is an isometric view of a connection instrument used to insert and remove the adapter of FIG. 4 into and out of the threaded central opening in the shell of an acetabular cup.

Referring to FIG. 7 there is shown a connection tool generally denoted as 200 including a handle 214, a shaft 212, a standard U-joint 216 and a connection socket 218. Connection socket 218 includes a multi-faceted connection 220 identical to multi-faceted connection 120 of FIGS. 6B and 6C. The purpose of tool 200 is to insert and remove adapter 24 from the central threaded hole 66 of shell 20.

Thus in use the surgeon would take shell 20 and threaded adapter 24 and, using tool 200, tighten the thread 28 of adapter 24 in threaded bore 66. This can also be done by hand. The surgeon would then connect either inserter/impactor 10 or 100 by inserting the connection end 30 of adapter 24 in to the socket 26. The surgeon can also put the adapter 24 into the cup bore by hand (and/or remove it by hand). The surgeon can also connect the impactor to the adapter 24 by hand. Thus connection elements 30 and 120 would engage to prevent the relative rotation between the adapter and the inserter/impactor. The surgeon would then impact anvil plate 16 or 106 after having placed shell 20 with adapter 24 mounted thereon in the correct position in the acetabular. After impaction the surgeon would remove impactor 10, 100 and then utilize tool 200 to remove the adapter 24 from shell 20. Because no force was transmitted through threads 28, removal is simple.

Furthermore, if the surgeon wishes to attach other tools to the shell/adapter combination, this can be done by providing tools with a similar socket and moving them in the axial direction so that they may be coupled with connection element 30 of adapter 24.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An acetabular cup insertion system for an acetabular cup having a threaded central opening and a part-spherical inner surface, the system comprising:
   an impactor having a strike plate at a first end thereof and a first connection element at a second end thereof;
   a longitudinally extending adapter having a threaded first end adapted to threadably engage the threaded opening in the acetabular cup, a second end of the adapter having a second connection element for engaging the impactor first connection element, an impaction flange extending radially outwardly of a longitudinal axis of the adapter, the flange having a first contact surface facing the second end of the adapter;
   a second contact surface surrounding the threaded first end of the adapter for contacting the part-spherical inner surface of the acetabular cup surrounding the threaded central opening, a distance between the first and second ends of the adapter being less than a distance between the part-spherical inner surface surrounding the threaded central opening and a rim of the acetabular cup surrounding the cup inner surface;
   wherein the first and second connection elements are corresponding multi-faceted connection elements;
   wherein the first connection element is located in a socket coupled to the impactor second end that receives the second end of the adapter; and
   wherein the socket has a base portion and an open end portion for receiving the second connection element of the adapter and at least partially receiving a shaft portion of the adapter, wherein the multi-faceted first connection element is located in the base portion of the socket.

2. The acetabular cup insertion system as set forth in claim 1 wherein the multi-faceted connection elements are polygonal in shape.

3. The acetabular cup insertion system as set forth in claim 1 wherein the adapter has a magnet received within a recess located adjacent the second end thereof.

4. The acetabular cup insertion system as set forth in claim 3 wherein the adapter is made of a non-magnetic material and the impactor is made of a magnetic material.

5. The acetabular cup insertion system as set forth in claim 1 wherein the impaction flange has a planar circular surface forming the first contact surface facing the second end of the adapter supported by a conical portion tapering inwardly towards a central axis of the adapter and towards the first end of the adapter.

6. The acetabular cup insertion tool as set forth in claim 5 wherein the conical portion terminates in an annular surface facing the adapter first end and forming the second contact surface.

7. The acetabular cup insertion system as set forth in claim 1 further comprising a driving tool having a U-joint with a connection element coupled thereto at a first end for connecting to the adapter second connection element for imparting a rotation to the adapter about a longitudinal axis thereof.

8. An acetabular cup insertion system for an acetabular cup having a threaded central opening and an inner surface, the system comprising:
   an impactor having a shaft with a strike plate at a first end thereof and a first connection element at a second end thereof, the first connection element having a first contact surface at an end thereof;
   an adapter having a threaded first end adapted to threadably engage the central opening in the acetabular cup and a second end with a second connection element thereon, the first end having a second contact surface for contacting the inner surface of the acetabular cup, the adapter having a third contact surface facing the second end of the adapter, such that upon engagement of the first and second connection elements the first and third contact surfaces engage; and
   wherein the adapter has magnet received within a recess located adjacent the second end thereof.

9. The acetabular cup insertion system as set forth in claim 8 wherein the first and second connection elements are corresponding multi-faceted connection elements.

10. The acetabular cup insertion system as set forth in claim 9 wherein the multi-faceted connection elements are polygonal in shape.

11. The acetabular cup insertion system as set forth in claim 9 wherein the first connection element is located in a socket coupled to the impactor second end that receives the second end of the adapter.

12. The acetabular cup insertion system as set forth in claim 11 wherein the socket has a base portion and an open end portion for receiving and at least partially receiving a shaft portion of the adapter, wherein the multi-faceted connection element is located in the base portion of the socket.

13. The acetabular cup insertion system as set forth in claim 8 wherein the adapter is made of a non-magnetic material and the impactor is made of a magnetic material.

14. The acetabular cup insertion system as set forth in claim 8 wherein an impaction flange has a planar circular surface forming the third contact surface facing the second end of the adapter supported by a conical portion tapering inwardly towards a central axis of the adapter and towards the first end of the adapter.

15. The acetabular cup insertion tool as set forth in claim 14 wherein the conical portion terminates in an annular surface facing the adapter first end and forming the second contact surface.

16. The acetabular cup insertion system as set forth in claim 8 further comprising a driving tool having a U-joint with a connection element coupled thereto at a first end for connecting to the adapter second connection element for imparting a rotation to the adapter about a longitudinal axis thereof.

17. An acetabular cup insertion system for an acetabular cup having a threaded central opening and a part-spherical inner surface, the system comprising:
   an impactor having a strike plate at a first end thereof and a first connection element at a second end thereof;
   a longitudinally extending adapter having a threaded first end adapted to threadably engage the threaded opening in the acetabular cup, a second end of the adapter having a second connection element for engaging the impactor first connection element, an impaction flange extending radially outwardly of a longitudinal axis of the adapter, the flange having a first contact surface facing the second end of the adapter;

a second contact surface surrounding the threaded first end of the adapter for contacting the part-spherical inner surface of the acetabular cup surrounding the threaded central opening, a distance between the first and second ends of the adapter being less than a distance between the part-spherical inner surface surrounding the threaded central opening and a rim of the acetabular cup surrounding the cup inner surface; and a driving tool having a U-joint with a connection element coupled thereto at a first end for connecting to the adapter second connection element for imparting a rotation to the adapter about a longitudinal axis thereof.

18. The acetabular cup insertion system as set forth in claim 17 wherein the first and second connection elements are corresponding multi-faceted connection elements, wherein the first connection element is located in a socket coupled to the impactor second end that receives the second end of the adapter, and wherein the socket has a base portion and an open end portion for receiving the second connection element of the adapter and at least partially receiving a shaft portion of the adapter, wherein the multi-faceted first connection element is located in the base portion of the socket.

19. The acetabular cup insertion system as set forth in claim 17 wherein the adapter has a magnet received within a recess located adjacent the second end thereof.

20. The acetabular cup insertion system as set forth in claim 19 wherein adapter is made of a non-magnetic material and the impactor is made of a magnetic material.

21. An acetabular cup insertion system for an acetabular cup having a threaded central opening and a part-spherical inner surface, the system comprising:

an impactor having a strike plate at a first end thereof and a first connection element at a second end thereof;

a longitudinally extending adapter having a threaded first end adapted to threadably engage the threaded opening in the acetabular cup, a second end of the adapter having a second connection element for engaging the impactor first connection element, an impaction flange extending radially outwardly of a longitudinal axis of the adapter, the flange having a first contact surface facing the second end of the adapter;

a second contact surface surrounding the threaded first end of the adapter for contacting the part-spherical inner surface of the acetabular cup surrounding the threaded central opening, a distance between the first and second ends of the adapter being less than a distance between the part-spherical inner surface surrounding the threaded central opening and a rim of the acetabular cup surrounding the cup inner surface;

wherein the first and second connection elements are corresponding multi-faceted connection elements;

wherein the first connection element is located in a socket coupled to the impactor second end that receives the second end of the adapter;

wherein the socket has a base portion and an open end portion for receiving the second connection element of the adapter and at least partially receiving a shaft portion of the adapter, wherein the multi-faceted first connection element is located in the base portion of the socket; and wherein the adapter has a magnet received within a recess located adjacent the second end thereof.

22. The acetabular cup insertion system as set forth in claim 21 wherein the adapter is made of a non-magnetic material and the impactor is made of a magnetic material.

23. An acetabular cup insertion system for an acetabular cup having a threaded central opening and an inner surface, the system comprising:

an impactor having a shaft with a strike plate at a first end thereof and a first connection element at a second end thereof, the first connection element having a first contact surface at an end thereof;

an adapter having a threaded first end adapted to threadably engage the central opening in the acetabular cup and a second end with a second connection element thereon, the first end having a second contact surface for contacting the inner surface of the acetabular cup, the adapter having a third contact surface facing the second end of the adapter, such that upon engagement of the first and second connection elements the first and third contact surfaces engage;

wherein the adapter has a magnet received within a recess located adjacent the second end thereof; and a driving tool having a U-joint with a connection element coupled thereto at a first end for connecting to the adapter second connection element for imparting a rotation to the adapter about a longitudinal axis thereof.

* * * * *